(12) United States Patent
Wozencroft (10) Patent No.: US 9,597,464 B2
(45) Date of Patent: Mar. 21, 2017

(54) AUTOINJECTOR WITH MEANS FOR PREVENTING REUSE AND DISCONNECTION OF SAID FIRST AND SECOND BODY PORTIONS AFTER OPERATION

(75) Inventor: Robert Wozencroft, Surrey (GB)

(73) Assignee: OWEN MUMFORD LIMITED, Oxford (GB)

( * ) Notice: Subject to any disclaimer, the term of this patent is extended or adjusted under 35 U.S.C. 154(b) by 830 days.

(21) Appl. No.: 13/997,481

(22) PCT Filed: Dec. 22, 2011

(86) PCT No.: PCT/GB2011/052558
§ 371 (c)(1),
(2), (4) Date: Aug. 7, 2013

(87) PCT Pub. No.: WO2012/085581
PCT Pub. Date: Jun. 28, 2012

(65) Prior Publication Data
US 2013/0331785 A1    Dec. 12, 2013

Related U.S. Application Data (60) Provisional application No. 61/425,995, filed on Dec. 22, 2010.

(30) Foreign Application Priority Data

Dec. 22, 2010 (GB) .................................. 1021735.4

(51) Int. Cl.
*A61M 5/00* (2006.01)
*A61M 5/50* (2006.01)
(Continued)

(52) U.S. Cl.
CPC ............ *A61M 5/50* (2013.01); *A61M 5/2033* (2013.01); *A61M 5/3204* (2013.01);
(Continued)

(58) Field of Classification Search
CPC ...... A61M 2005/2073; A61M 2205/27; A61M 5/2033; A61M 5/50; A61M 2205/273
(Continued)

(56) References Cited

U.S. PATENT DOCUMENTS

2007/0112310 A1    5/2007   Lavi et al.

FOREIGN PATENT DOCUMENTS

| EP | 1 683 537 | 7/2006 |
|---|---|---|
| GB | 2452030 | 2/2009 |

(Continued)

OTHER PUBLICATIONS

JP Office Action, dated Nov. 10, 2015; Application No. 2013-545503.
(Continued)

*Primary Examiner* — Deanna K Hall
(74) *Attorney, Agent, or Firm* — Young & Thompson (57) ABSTRACT

An autoinjector has a body portion (10, 12) containing a syringe (13) or cartridge with a needle at its forward end, the autoinjector having a drive arrangement (60 . . . ) for effecting operation of the autoinjector and including a drive element that moves from a first position to a second position during the operation, the body including a first (10) and a second body portion (12) connected together by a snap fit arrangement including a resiliently moveable latch finger (138) on one of the body portions that cooperates with a latch surface (142) on the other thereof to hold the two portions connected, wherein the drive element in the second position (60) limits or prevents resilient movement of the (Continued)

moveable latch finger (142), thereby preventing disconnection of the first and second body portions after operation.

20 Claims, 10 Drawing Sheets

(51) Int. Cl.
*A61M 5/20* (2006.01)
*A61M 5/32* (2006.01)

(52) U.S. Cl.
CPC .............. *A61M 2005/206* (2013.01); *A61M 2005/2073* (2013.01); *A61M 2205/27* (2013.01)

(58) Field of Classification Search
USPC ........................................ 604/110
See application file for complete search history.

(56) References Cited

FOREIGN PATENT DOCUMENTS

| | | | |
|---|---|---|---|
| GB | 2 463 034 | 3/2010 | |
| GB | WO 2010125400 A2 * | 11/2010 | .......... A61M 5/2033 |
| JP | 2006-204918 | 8/2006 | |
| WO | 2005/009515 | 2/2005 | |
| WO | 2009-137486 | 11/2009 | |
| WO | 2010/125400 | 11/2010 | |
| WO | 2010/127146 | 11/2010 | |
| WO | 2010/139636 | 12/2010 | |

OTHER PUBLICATIONS

International Search Report dated Apr. 18, 2012, corresponding to PCT/GB2011/052558.
British Search Report dated Mar. 11, 2011, corresponding to the Foreign Priority Application No. GB1021735.4.

* cited by examiner

AUTOINJECTOR WITH MEANS FOR PREVENTING REUSE AND DISCONNECTION OF SAID FIRST AND SECOND BODY PORTIONS AFTER OPERATION

BACKGROUND OF THE INVENTION

This invention relates to autoinjectors.

DESCRIPTION OF THE RELATED ART

Many autoinjectors are assembled by inserting a syringe or cartridge into a front body assembly and then snap-fitting the front assembly containing the syringe or cartridge to a rear body assembly containing a drive arrangement. For safety and other purposes, it is highly desirable to make it difficult if not impossible for the device to be disassembled after use.

SUMMARY OF THE INVENTION

Accordingly, in one aspect, this invention provides an autoinjector having a body portion containing a syringe or cartridge with a needle at its forward end, the autoinjector having a drive arrangement for effecting operation of said autoinjector and including a drive element that moves from a first position to a second position during said operation, said body including a first and a second body portion connected together by a snap fit arrangement including a resiliently moveable latch finger on one of said body portions that cooperates with a latch surface on the other thereof to hold the two portions connected, wherein said drive element in said second position limits or prevents resilient movement of said moveable latch finger thereby preventing disconnection of said first and second body portions after operation.

Preferably first and second body portions comprise front and rearward generally tubular body portions that are snap fitted together during assembly.

In many embodiments said snap fit arrangement includes a plurality of respective removable latch fingers and latch surfaces, and said drive element conveniently blocks at least two of said resiliently moveable latch fingers when in said second position. The latch surface may comprise an edge of a latch through hole. Conveniently, said drive element is an elongate plunger having a blocking surface for moving into alignment with the or each resiliently moveable latch finger when in said second position.

Whilst the invention has been described above, it extends to any inventive combination or sub-combination of novel features set out above, or in the following description or claims.

BRIEF DESCRIPTION OF THE DRAWING FIGURES

The invention may be performed in various ways and an embodiment thereof, with various modifications, will now be described by way of example only, reference being made to the accompanying drawings in which.

DETAILED DESCRIPTION OF THE INVENTION

Figure 1:
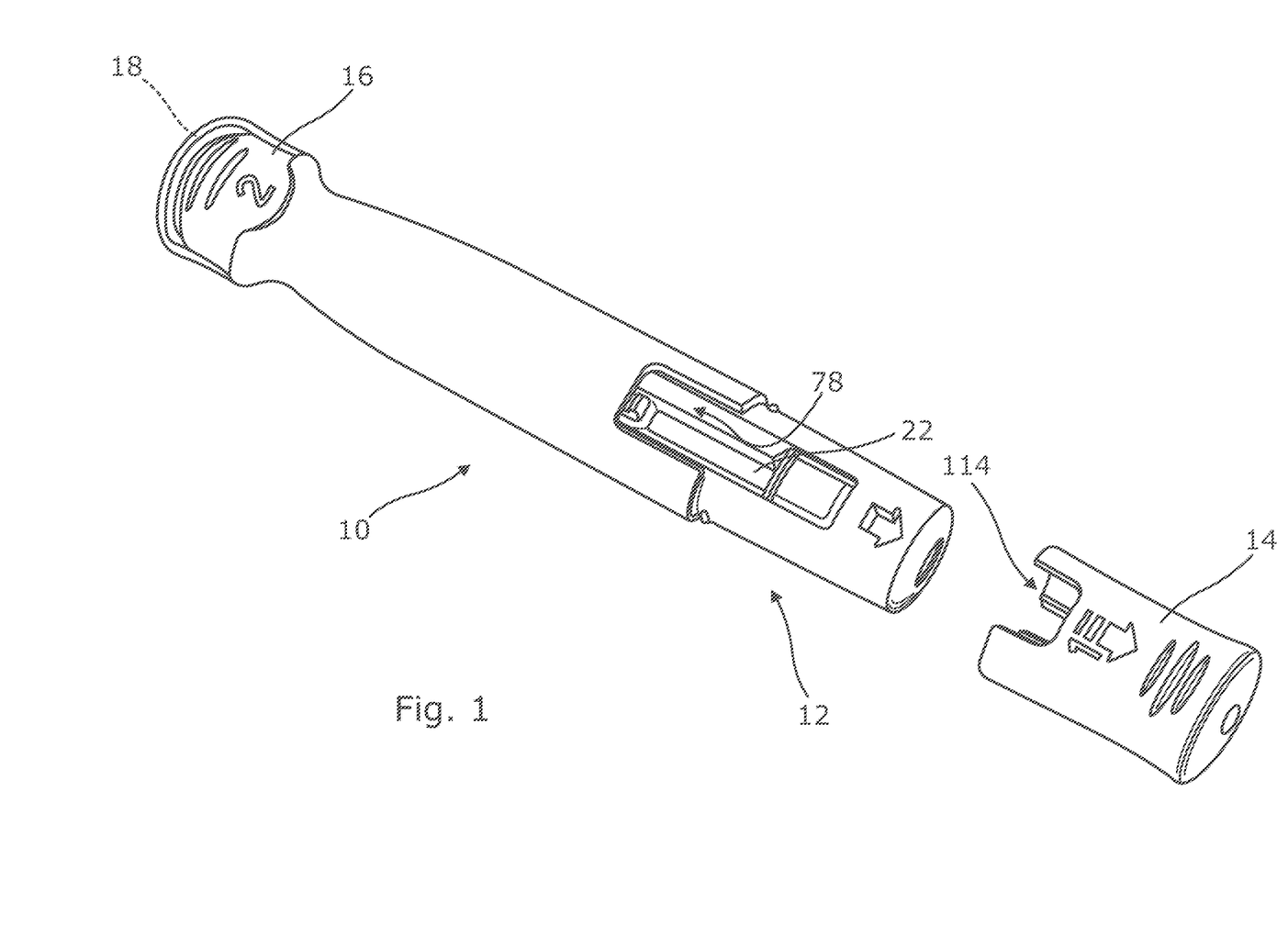
FIG. 1 is a perspective view of an autoinjector in accordance with an embodiment of this invention with the first, front cap removed prior to an injection, but before removal of the second, rear cap.
Figure 2:
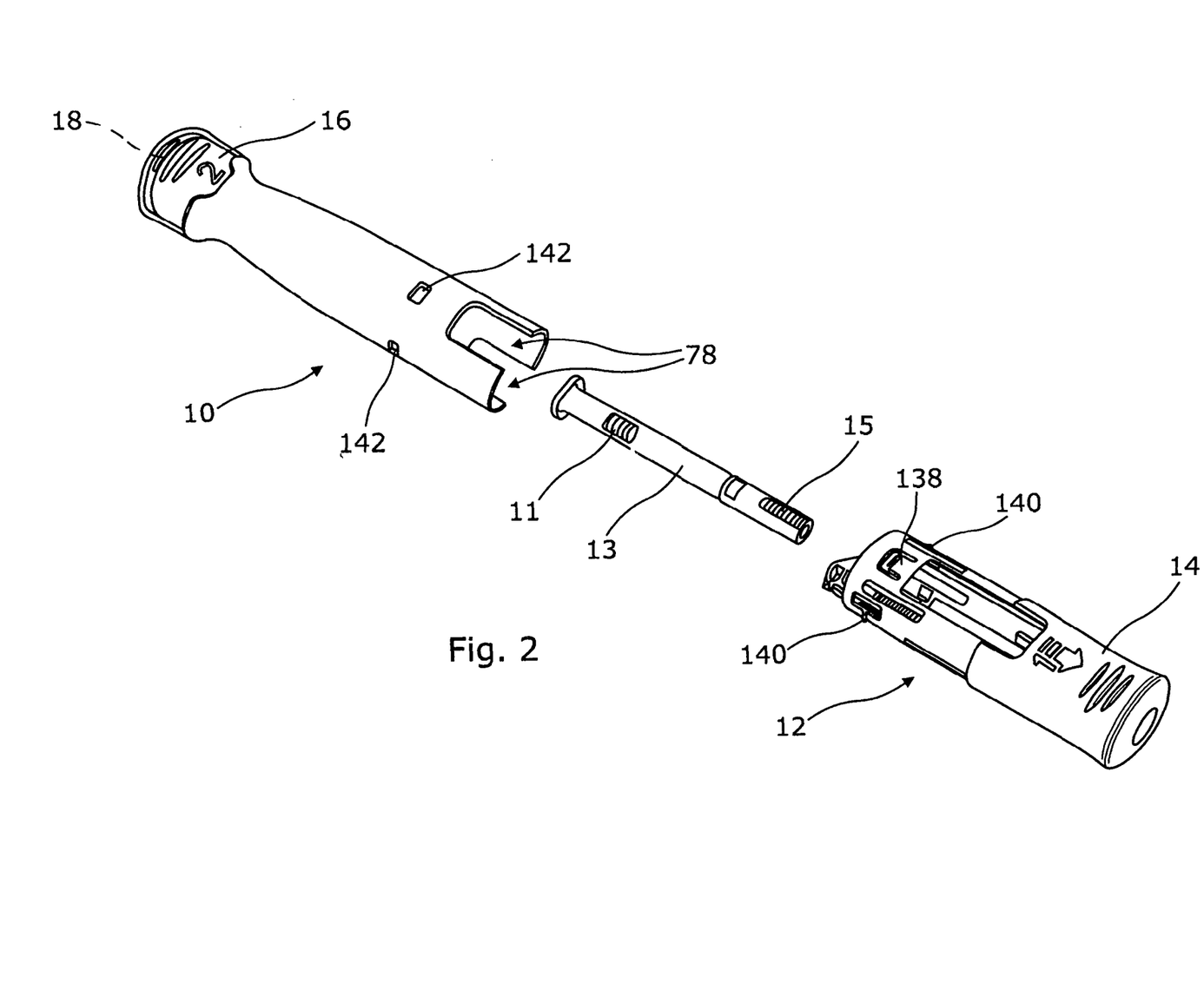
FIG. 2 is a view of the autoinjector with the rear assembly and front assembly separate prior to loading of a syringe in the forward assembly and being snap-fitted together.

The embodiment of autoinjector illustrated in the Figures and described below is designed automatically to inject a selected dose of medicament when offered up an injection site and fired. Referring initially to FIGS. 1 and 2, the autoinjector comprises a rear assembly 10 containing a drive mechanism and a front assembly 12 for receiving a syringe 13 with medicament. The front and rear assemblies are snap-fitted together during manufacture. On the front end of the device is a removable cap 14 that also serves as needle shield remover as to be described below. On the rear end of the rear assembly is a rear cap 16 which includes a safety pin which prevents premature firing of the drive mechanism, the rear cap also covering the firing button 18.

Figure 3:
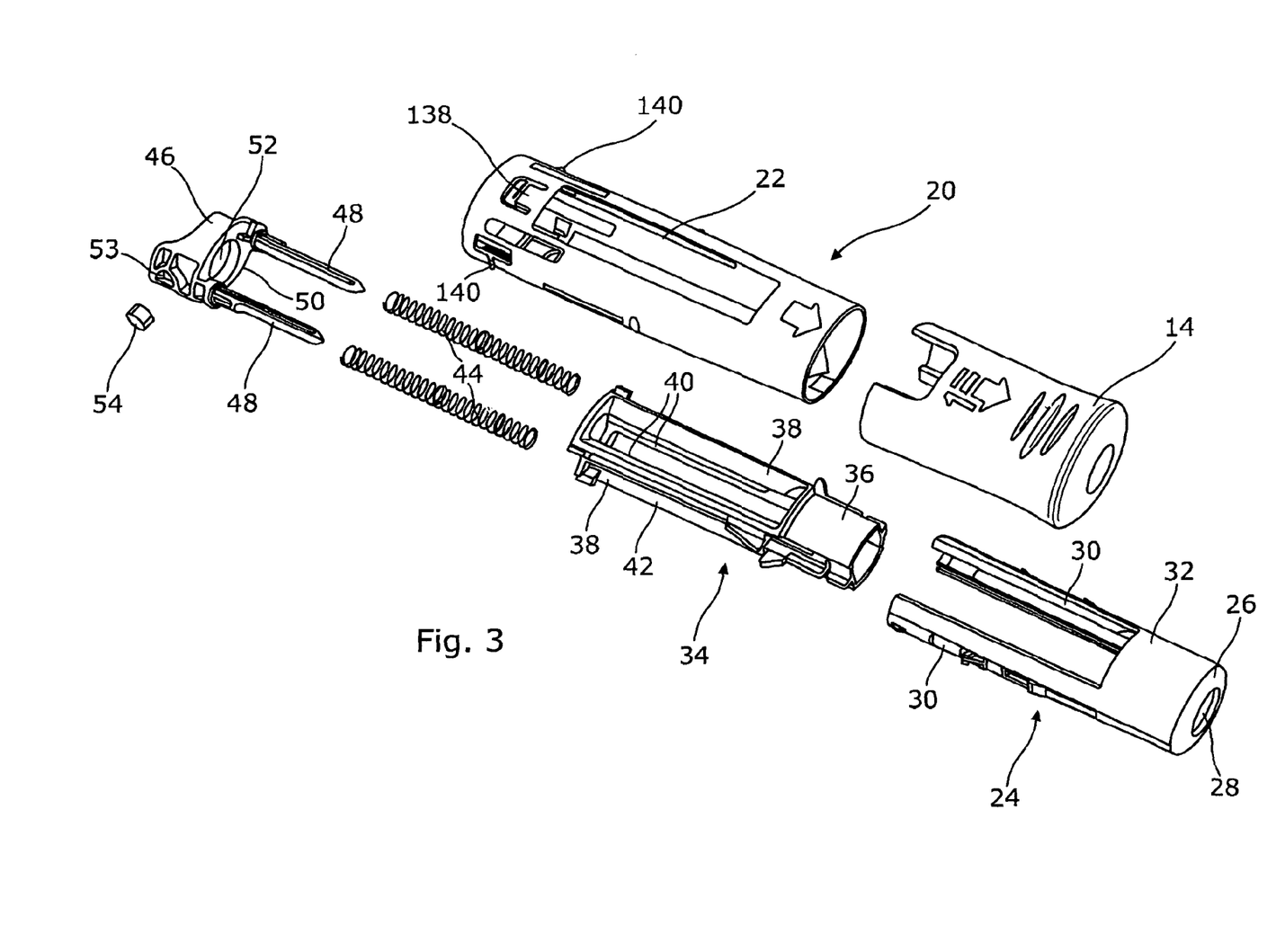
FIG. 3 is an exploded view of the front assembly.

Referring now to FIG. 3, the front assembly 12 comprises an outer body housing 20 of generally clear plastic material defining opposed integral viewing windows 22 through which the syringe can be viewed when the device has been assembled. The windows allow the whole of the dose volume of the syringe to be viewed. Apart from the clear plastic material of the windows 22, the body housing 20 may be opaque. Provision of a transparent window element, instead of the common arrangement of an open aperture or slot, has the advantage of preventing external access to the syringe. Also the provision of twin shroud springs spaced to either side of the longitudinal axis of the device means that the entire length of the dose volume is clearly visible without being obscured by any springs etc.

Slideably mounted within the housing 20 is a needle shroud 24 having a chamfered, conical and/or convexly curved domed front face 26 with a central aperture 28 therein to provide a forwardly dished configuration through which the needle of the syringe may project during the injection. The shroud 24 includes two rearwardly extending arms 30 of arcuate cross-section, extending back from a forward tubular section 32.

Slideably coupled to the needle shroud is a syringe carrier 34 having a forward tubular portion 36 capable of sliding telescopically inside the tubular portion 36 of the needle shroud 24. Extending rearwardly from the tubular portion 36 of the syringe carrier 34 are two arms 38 having opposed inner concave surfaces 40 for slideably receiving the barrel of a syringe and outer concave surfaces 42 for defining with convex inner arcuate surfaces on the arms 30 of the needle shroud 24, cylindrical containment spaces for a pair of shroud springs 44.

A spring guide 46 has two forwardly extending fingers 48 that pass down the centre of a respective spring 44. The spring guide 46 has an over-moulded liner 50 surrounding a circular aperture 52 through which a syringe is passed. The liner serves as a shock absorber for the syringe. The spring guide 46 is a snap fit with the rear end of the syringe carrier 34 as to be described below. The spring guide 46 has a rearwardly extending tubular portion in one side wall of which is a recess 53 for captively receiving a disc magnet 54.

Figure 4:
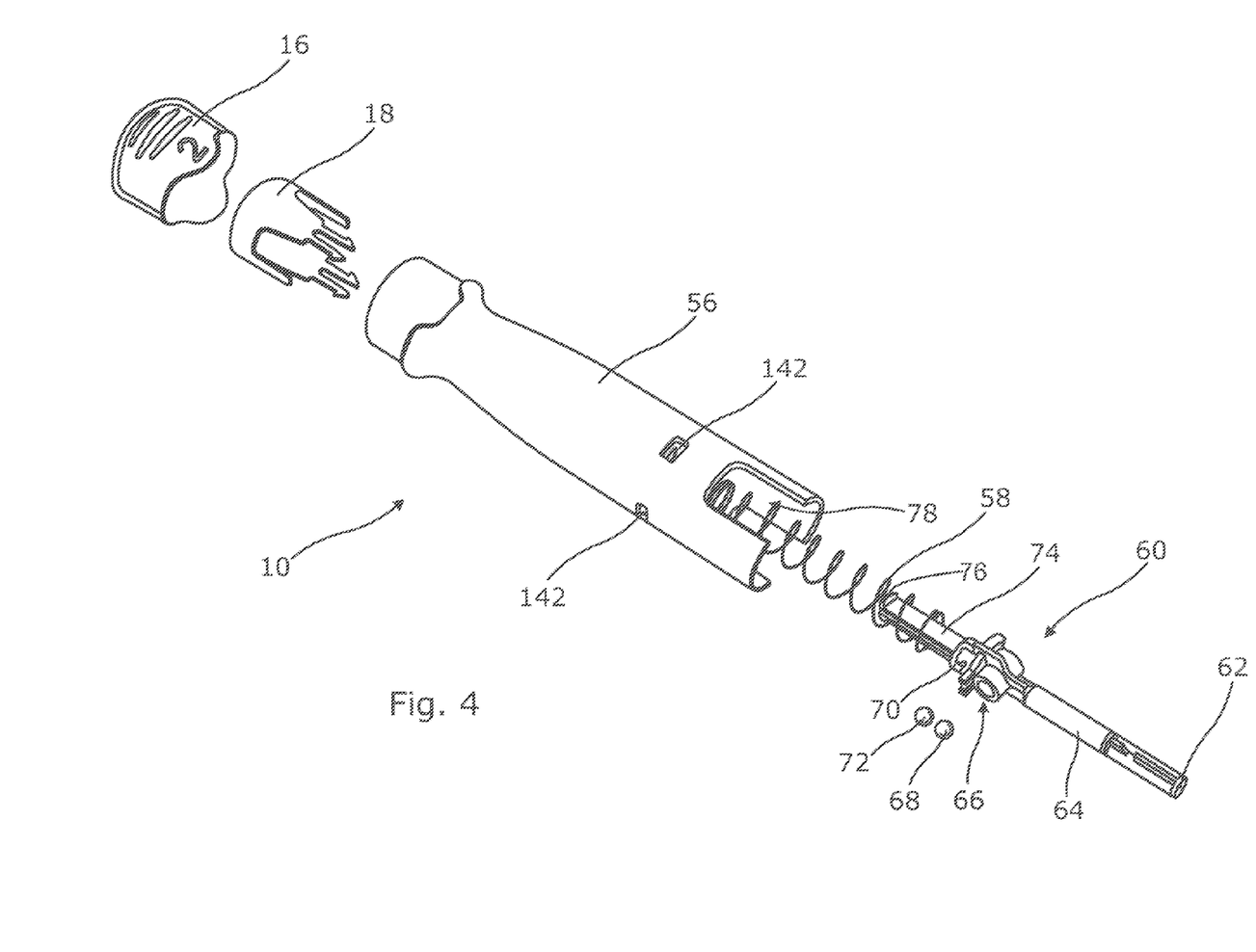
FIG. 4 is an exploded view of the rear assembly.
Figure 5:
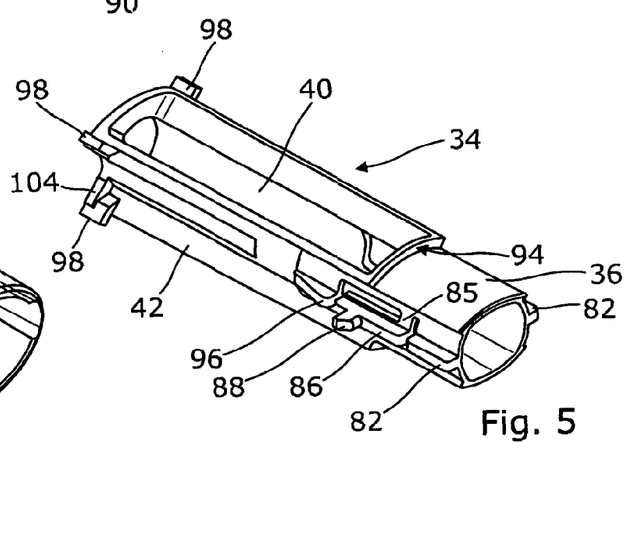
FIG. 5 is an enlarged view of the syringe carrier.
Figure 6:
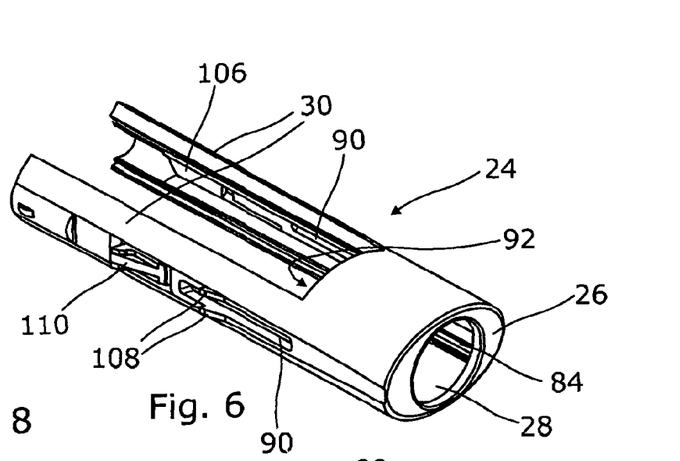
FIG. 6 is an enlarged view of the needle shroud.
Figure 7:
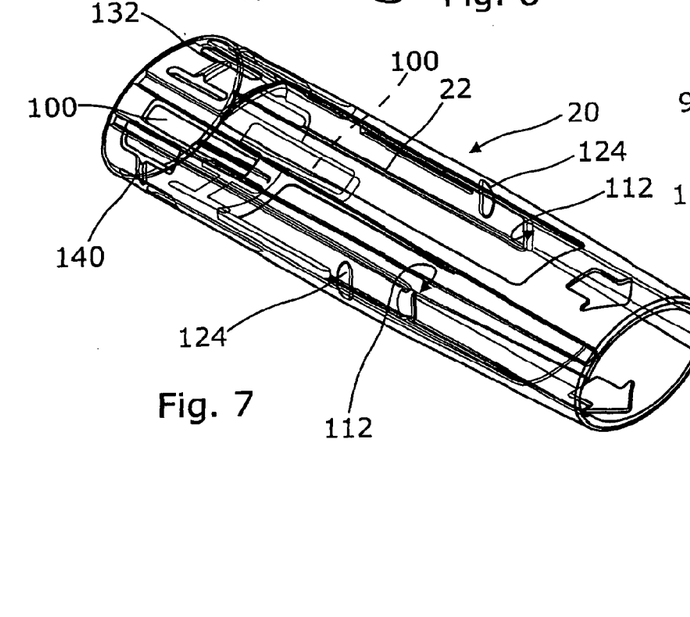
FIG. 7 is an enlarged view of the front body housing.

Referring now to FIG. 4, the rear assembly comprises a rear body housing 56 in which is received the main drive spring 58 which acts on the rear end of a plunger 60. The plunger has a forward end 62 for engaging the piston 11 within a syringe and an over-moulded coloured indicator strip 64. To the rear of the indicator strip 64 is a transverse passage 66 in which is mounted for transverse movement a ball magnet 68. To the rear of the passage 66 is a provided a recess 70 which receives a ferro-magnetic keeper ball 72 which is fixedly disposed on the longitudinal axis of the plunger 60. The plunger 60 has two rearwardly extending split arrowhead limbs 74 with barbs 76 on the rear ends which seat around the edge of an annular catchment surface 77 in the inside of the rear body housing 56 (see FIGS. 14 and 15) to latch the plunger in a cocked position, with the main spring 58 compressed.

The autoinjector is of modular construction designed to allow all except two components to be the same for autoinjectors with syringes of three different fill volumes. The shape and the size of the syringe itself is standard; only the fill volume is different. The two components that vary are the rear body housing 10 and the plunger 60. The forward end of the rear body housing 52 contains opposed cut outs or slots 78 which are of variable length according to the fill volume contained in the syringe. The axial length of the slots 78 in the rear body housing 56 is proportional to the fill volume. Also the indicator position moves by the same amount so that it arrives at the same place relative to the body at the end of the plunger stroke. The plunger is also modified according to the fill volume of the syringe to locate the magnet-containing passage 66 so that, at the end of its forward stroke, it reaches the same axial position with respect to the rear body housing 56 for each fill volume. In other words, the plunger 60 and the axial length of the slots 78 are designed so that, for each of the plurality of fill volumes, the user will see prior to use in the viewing window 22 just that length of the syringe containing the dose, with the window being framed at the rear end by the slots 78. After the dose has been delivered, the indicator will be at the same forward position for each fill volume.

Referring now to FIGS. 5 to 9, the assembly of the principal components of the front assembly will be described in more detail. The syringe carrier 34 has twin linear ribs 82 provided to either side of the forward tubular portion 36. The ribs 82 run in respective channels 84 on the inside of the tubular portion 32 of the needle shroud. Immediately behind each rib 82 is a live hinge 85 from which extends back a spring finger 86 with a barb 88 with a rearwardly inclined forward surface. When the syringe carrier is assembled telescopically into the needle shroud 24, the barbs 88 project through slots 90 in the shroud 24 (see FIG. 6) to limit forward movement of the shroud 24 relative to the syringe carrier 34 when the rear ends of the slots 90 contact the barbs 88. Rearward movement of the shroud 24 relative to the syringe cap is limited by a rearward shoulder 92 of the needle shroud tubular portion abutting a forward facing shoulder 94 upstanding from the rear of the tubular portion 36 of the syringe carrier 34. Rearwardly of the barbs 88 on the syringe carrier are two rearwardly facing ramp surfaces 96.

Figure 8:
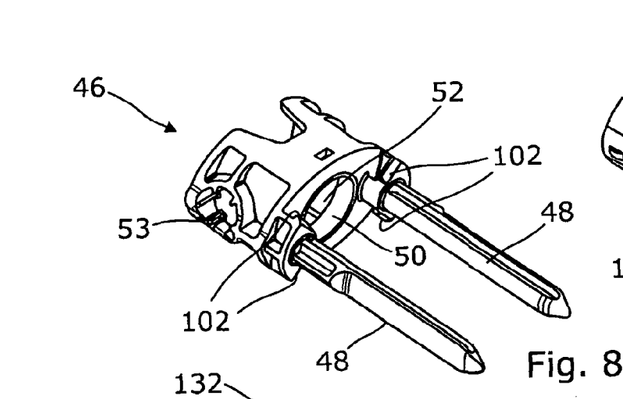
FIG. 8 is an enlarged view of the spring guide.
Figure 9:
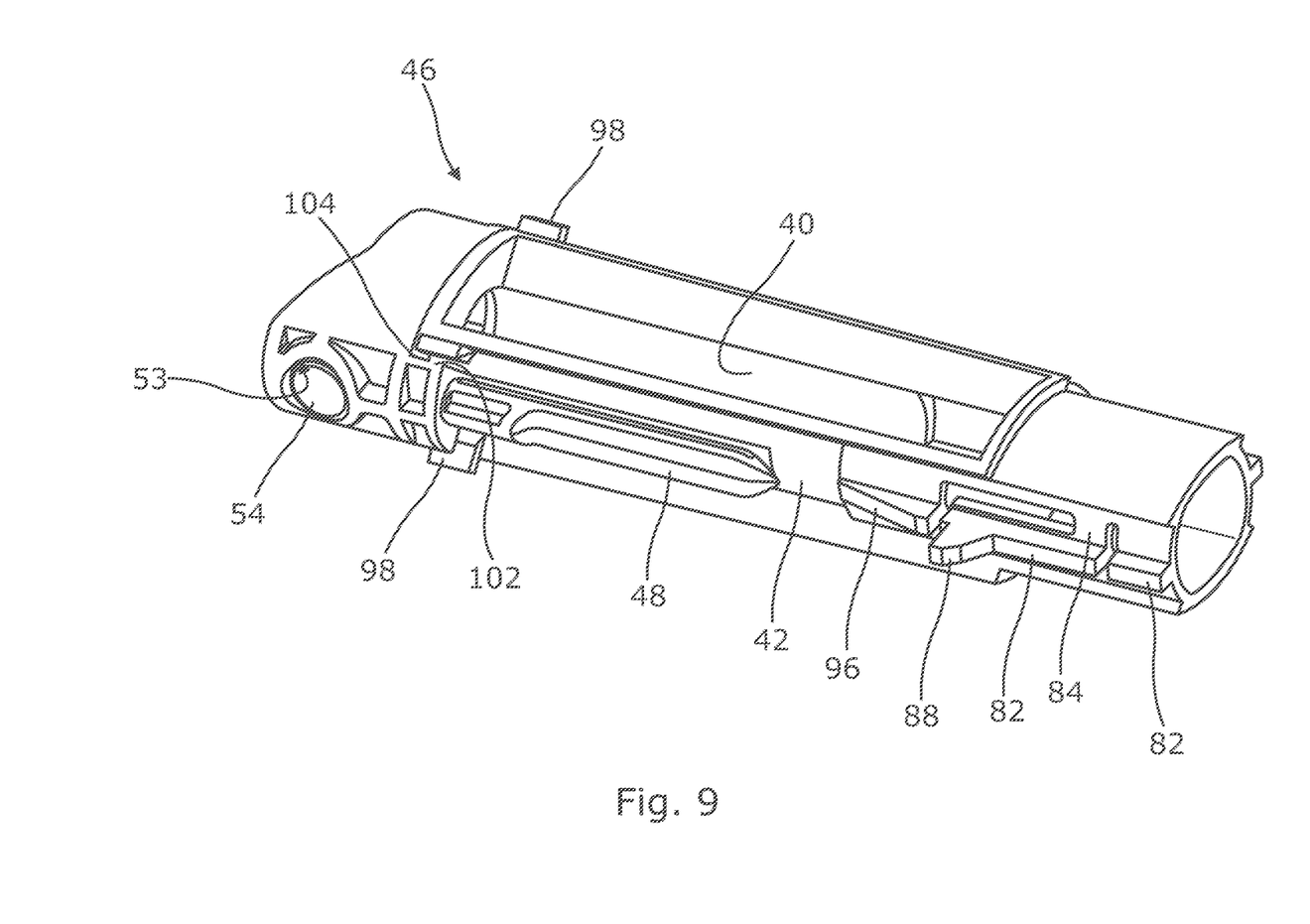
FIG. 9 is a view showing the spring guide and syringe carrier snap-fitted together.

At its rear end, the syringe carrier has four lugs 98 that, when the device is assembled, run in respective slots 100 in the front body portion 20 to limit linear movement of the syringe carrier relative to the front body portion 20. Snap fitted onto the rear of the syringe carrier is the spring guide 46 as shown in FIG. 8. This has snap fit tabs 102 that snap fit around walls 104 on the rear end of the syringe carrier. The tabs also form a platen surface for the shroud springs 44, with the spring guide fingers 48 passing down the centre thereof. The forward ends of the shroud springs are seated on projecting fingers 106 towards the rear of the arms 30 of the needle shroud 24. About two-thirds of the way back from the front of each slot 90 are two barbs 108 with inclined forward surfaces. Behind each slot 90, on a live hinge is a rearward barb 110, again with an inclined forward surface. The barbs 108 and 110 cooperate with respective opposed barbs 112 about a third of the way down the length of the front body housing 20 on the inner walls thereof.

Figure 14A:
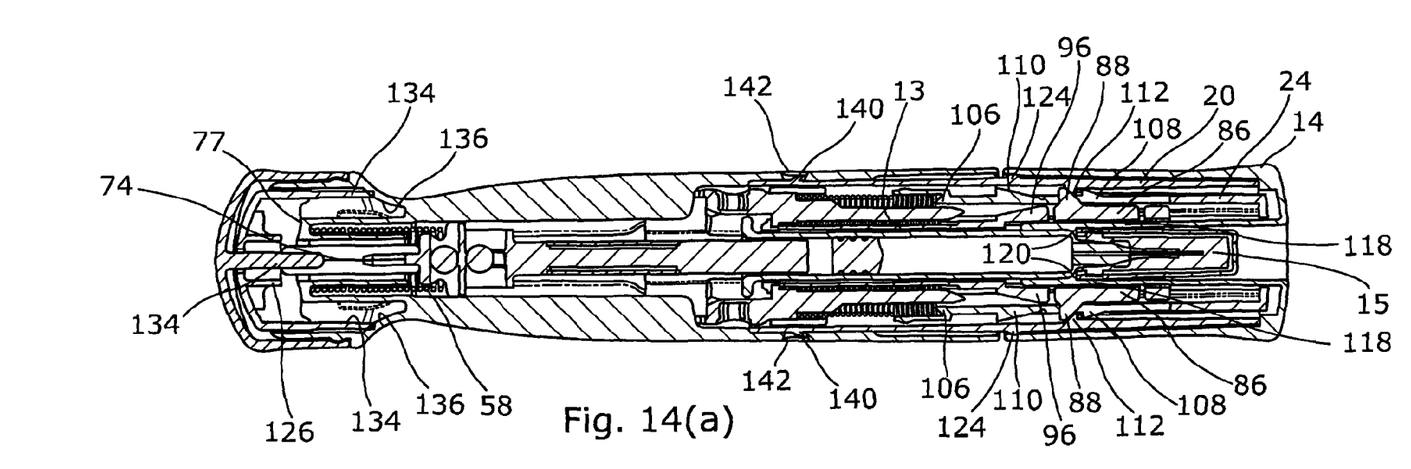
FIGS. 14(a) and (b) are transverse section views on the major and minor planes respectively of the autoinjector when in its pre-use condition.
Figure 14B:
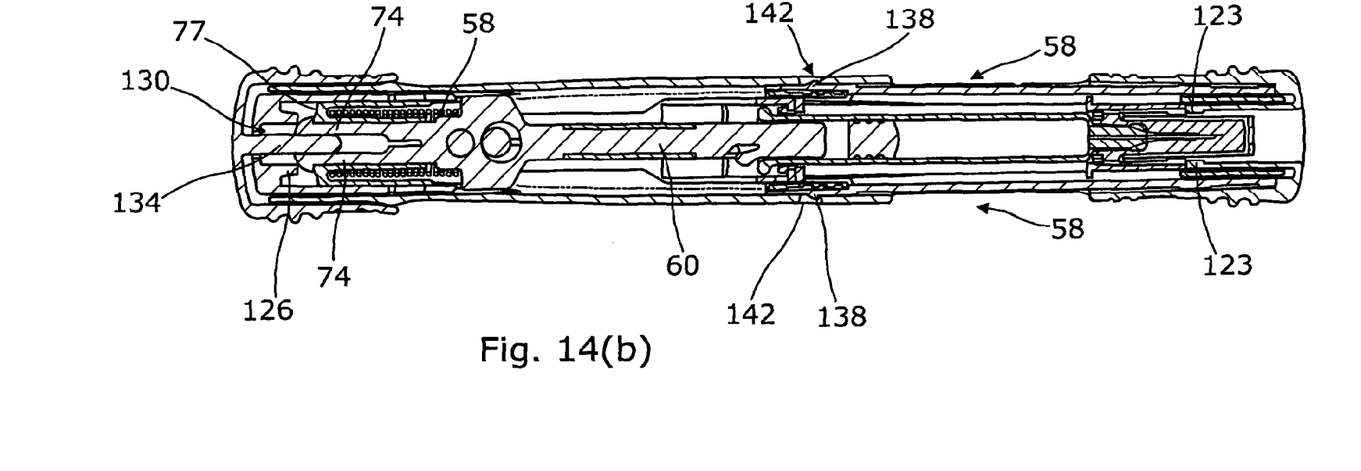

The arrangement of the barbs in the pre-use position can be clearly seen in FIGS. 14 and 15. In the pre-use position, the barbs 108 on the needle shroud cooperate with the barbs 112 on the front body housing to prevent rearward movement of the needle shroud 24. The forward faces of the barbs 88 on the syringe carrier also cooperate with the barbs 112 on the front body housing on the forward housing to prevent forward movement of the syringe carrier 34 prior to and during removal of the front cap 14. Removing the cap removes a bracing on the barbs 88 which initially prevents inward movement of the barbs so that, when fired, the force of the drive spring causes the barbs 88 to cam past the barbs 112 on the front body housing. During operation of the device, when fired, with the needle shroud 24 held against forward movement by its contact with the skin around the injection site, the sub-assembly of the syringe 13 and the syringe carrier 34 is shifted forwardly, relative to the forward housing to a limit position defined by the lugs 98 reaching the forward ends of the slots 100. After the injection is complete, the needle shroud 24 moves forward as the skin contact pressure is removed from the surface 28 as the device is lifted clear of the skin. This allows the needle shroud to move forwardly under the influence of the shroud springs 46 so that the rear barbs 110 move forwardly and snap past the barbs 112 on the front housing 20 to prevent retraction once the needle shroud has extended. The barbs 110 are braced in this position by the underlying ramp surfaces 96 on the syringe carrier 34.

Figure 10:
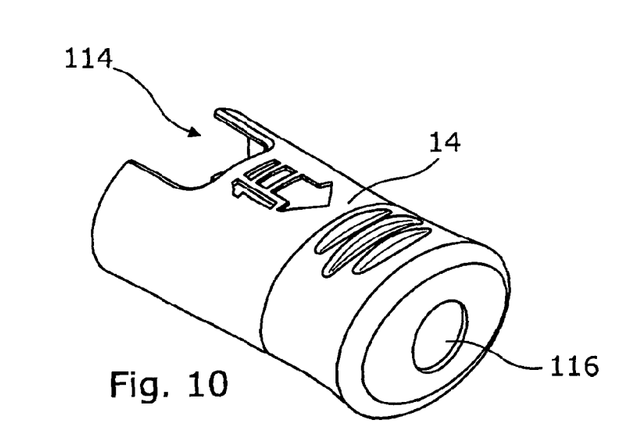
FIG. 10 is an enlarged view of the front cap/needle shield remover.
Figures 11, 13:
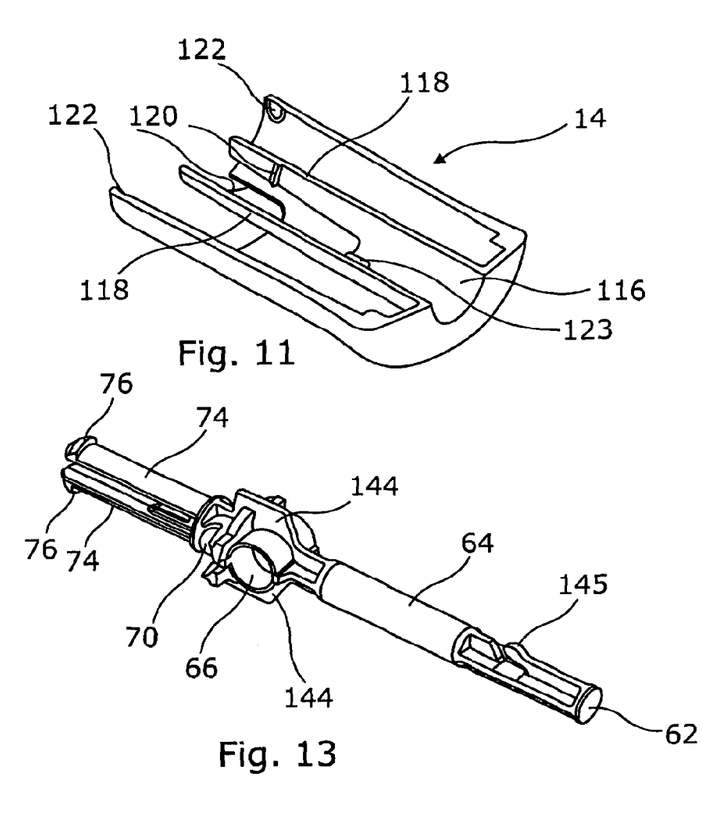
FIG. 11 is a horizontal section view taken through the cap of FIG. 10 on the major axis thereof.
FIG. 13 is an enlarged view of the plunger.

Referring now to FIGS. 10 and 11, the removable front cap 14 has opposed slots 114 which align with the slots 78 on the rear body housing 56, to frame the window 22 in the front body housing 20 to allow viewing of the dose volume as described above. Referring more particularly to FIG. 11, the cap is elliptical in outer section and has an inner central cylindrical portion 116 extending rearwardly from which extend further two fingers 118 of arcuate cross-section disposed on the major axis of the ellipse. On the inner surface of the fingers, towards the rear ends, are respective inwardly directed barbed ribs 120 with inclined rear surfaces. As seen in FIGS. 14 and 15, the ribs 120 are designed to snap into a gap formed between the forward shoulder on the barrel of the syringe 13 and the rear surface of the rigid needle shield 15 or an aperture therein. When the syringe 13 is loaded into the front assembly 12 (with the cap 14 attached) during manufacture, the rigid needle shroud 15 snaps past the ribs 120 so that they lodge behind the rear edge of the needle shield 15 (or a rear edge of an aperture in the needle shield) as shown. The front cap 14 also has twin shallow scallops 122 which releasably engage pips 124 on the outer surface of the front body housing when the cap is fitted (see FIGS. 14 and 15).

When in the condition as supplied (FIG. 14) the fingers 118 of the cap underlie the spring fingers 86 on the syringe carrier 34 and prevent these from flexing inwardly. In this condition, the fingers 118 thus brace the spring fingers 86 against inward unlatching motion. The forward end of the cylindrical portion 116 of the cap 14 is also provided with inward projections 123 aligned with the minor axis of the ellipse and which prevent forward movement of the rigid needle shield relative to the front cap 14. In this way, when the front cap 14 is withdrawn from the position shown in FIG. 15, the ribs 120 pull the rigid needle shield 15 to ease it off the forward end of the syringe 13. At the same time the presence of the fingers 118 also temporarily locks the syringe carrier 34 (and thus the syringe 13) against forward movement by blocking the fingers 86 against inward movement until the needle shield is off the syringe to prevent the syringe from being pulled forwardly if there is a tight fit between the syringe and the needle shield. When the front cap is free of the device the needle shield 15 is captive in the cap 14, trapped by the ribs 120 and the inward projections 123. Orienting the ribs 120 and the inward projections 123 at 90° means that the open ended cap may be injection-moulded in a simple injection mould with a slide rather than requiring a more complex mould design.

Figure 12:
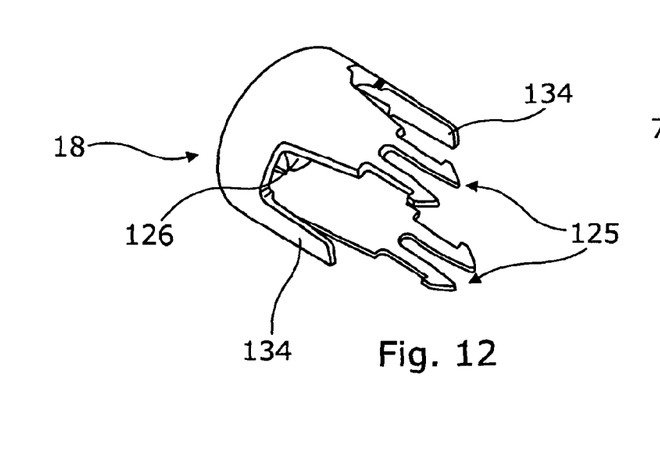
FIG. 12 is an enlarged view of the trigger button.
Figure 15A:
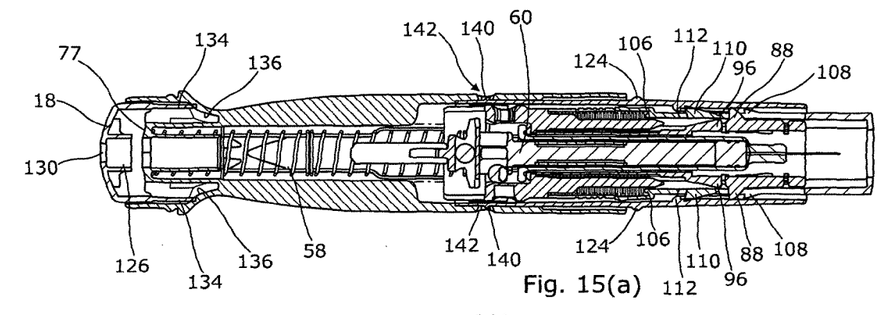
FIGS. 15(a) and (b) are transverse section views on the major and minor planes respectively of the autoinjector after use, and FIGS. 16(a) and (b) are detail views on the front end of the device showing the forwardly dished skin-contact surface.

Referring to FIGS. 4, 12 and 15, the firing button 18 is of elliptical form with two split arrowhead tabs 125 aligned with the minor axis, which seat behind respective ribs on the inner rear surface of the rear housing portion 56 to retain the firing button 18 on the rear of the housing and to limit rearward movement thereof. The inner rear surface of the trigger has a firing boss 126 which is of slightly smaller diameter than the outer diameter of the split arrowheads 74 on the rear of the plunger 60 so that, when the firing button 18 is pressed forwardly from the position shown, the boss squeezes the twin arrowheads 74 together to release the barbs 76 from the catchment surface 77 to free the plunger for forward movement. The firing button 18 has an aperture 130 concentric with the boss 126 through which a safety pin 134 on the rear cap 16 passes to hold the split arrowheads apart. Aligned with the major axis of the ellipse are two forwardly extending flexible biasing strips 134 which cooperate with respective bias camming surfaces 136 in the rear end of the rear housing 56, as shown in FIGS. 14(a) and 15(a) to provide a low friction gliding plastic-to-plastic surface contact. The camming surfaces 136 are shaped to provide a predetermined variation of resistance force with distance. The biasing strips cooperate with the curved rear portion of the camming surfaces to provide a bias force tending to restore the button to its rearmost position as defined by the split arrowhead tabs. It is desirable to provide a tactile resistance to movement and to require a few millimeters of movement before the firing boss 126 releases the plunger, to avoid premature firing. A forward portion of the camming surfaces is of shallower inclination and designed to provide a non-reversible resistance to movement after the device has been fired, thereby to trap or wedge the firing button in its forwardmost position. This gives a further useful visual cue to a user as to whether the device has been fired or not. Of course, if required the camming surface may instead be designed to return the button to its original position after firing.

Figure 15B:
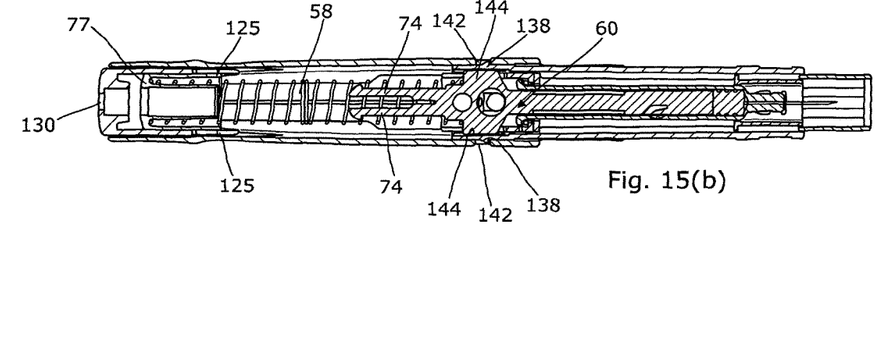
Figures 16A, 16B:
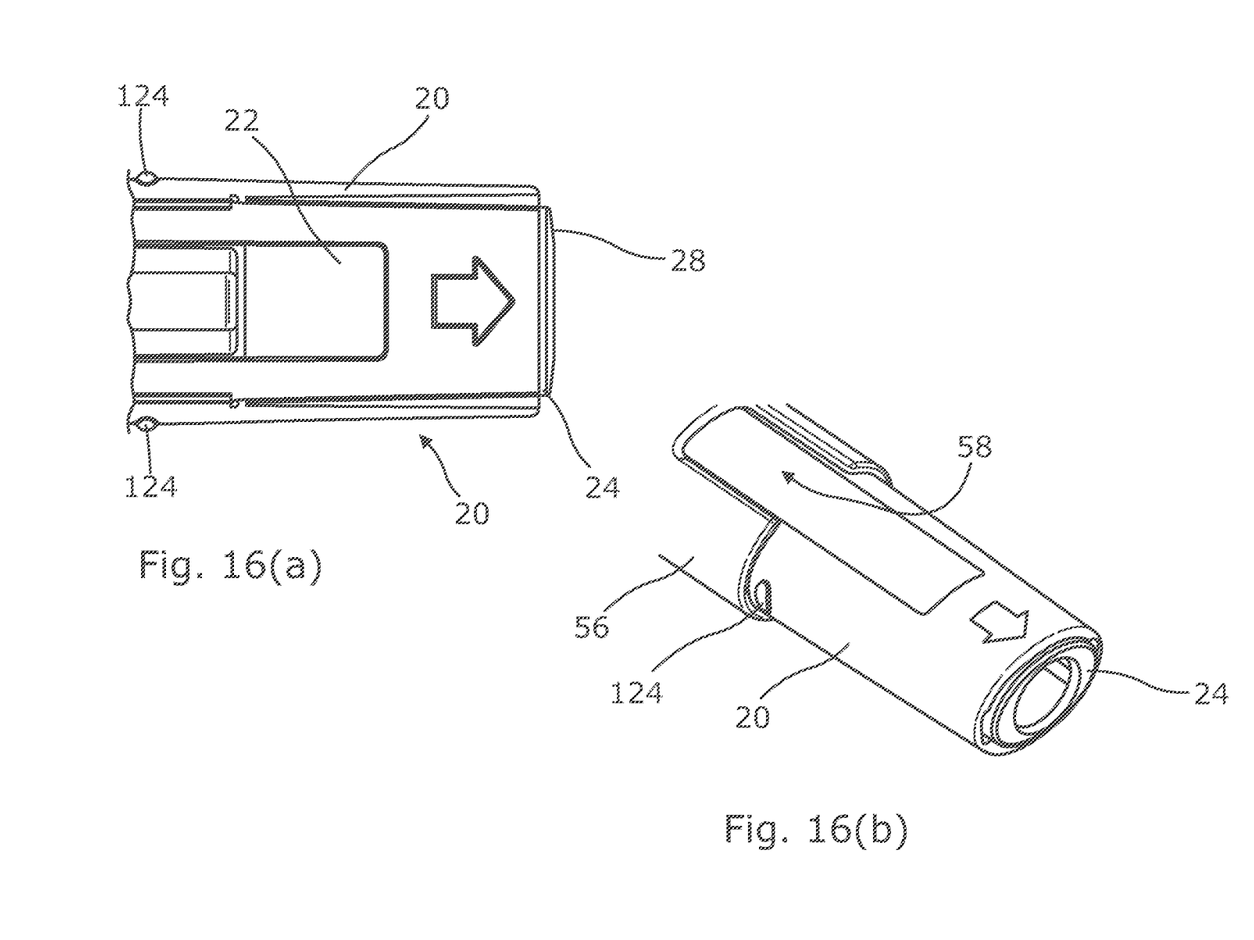

The autoinjector as illustrated includes several safety features to prevent inadvertent firing and to render the device safe after use. It is also highly desirable to resist or prevent disassembly of the device after use. It will be noted from the description and FIG. 2 above that the device is assembled by inserting a syringe into the syringe carrier in the front assembly and then snap-fitting the front and rear assemblies together. The snap fitting is done by means of outwardly facing sprung tabs 138, 140 on the rear of the front body housing 20 which seat simultaneously in respective apertures 142 in the rear body housing 56. One pair of tabs 138 is aligned with the minor axis and one pair 140 with the major axis of the device. It will be appreciated that, given appropriate dexterity and strength, it would be possible to press in all four of the tabs 138, 140 by poking an implement through the recesses 142 from outside and thereby disassemble the device. However, this is prevented in this embodiment by means of two fin formations 144 provided on the plunger 60 as seen in FIGS. 13 and 15(b). The plunger is designed so that, once the device is fired and the plunger is at its post-firing position, the fin formations 144 underlie the tabs 138 on the minor axis of the ellipse, as shown in FIG. 15(b), thereby bracing them against inward deflection and preventing disassembly.

For operation, the user removes the front cap 14 and rear cap 16, thereby arming the device. The device is then offered up to the injection site to press the conical or curved front face of the needle shroud 26 against their skin. When ready, the firing button 18 is pressed, which releases the plunger 60 for forward movement under the action of the main drive spring 58. Initially, due to a sprung engagement finger 145 on the plunger, the plunger and syringe move as one forwardly to extend the needle to penetrate the flesh, with this movement continuing until the lugs 98 on the syringe carrier reach the forward end of the slots 100 on the front body housing, thereby inserting the syringe needle to the required depth. Upon arresting movement of the syringe, the sprung engagement finger 145 flexes inwardly into the bore of the syringe and the plunger continues to move, driving the piston 11 down the syringe body to expel a dose. Alternatively, in other designs of the device, the spring engagement finger may yield so that the plunger starts to move into the syringe before forward movement of the latter is arrested. In either design, when the plunger reaches its forwardmost position, the ball magnet 68 which up till now has been held in the passage 66 on the centre line of the plunger by magnetic attraction to the keeper ball 72 is attracted by the greater force provided by the disc magnet 54 held in the recess of the spring guide, accelerating towards it and impacting the magnet and/or spring guide to produce a loud audible click to indicate to the user that the injection is complete.

The user then removes the device from their skin and the release of pressure on the front end of the needle shroud 24 means that it can now extend forwardly under the influence of the twin shroud springs 44 to move forwardly to shield the needle. As it nears its forwardmost position, the barbs 110 snap past the barbs 112 on the inside of the front housing 20 thereby to prevent retraction of the needle shroud.

The invention claimed is:

1. An autoinjector having a body portion containing a syringe or cartridge with a needle at its forward end, the autoinjector having a drive arrangement for effecting operation of said autoinjector and including a drive element that moves from a first position to a second position during said operation, said body including a first and a second body portion connected together by a snap fit arrangement including a resiliently moveable latch finger on one of said body portions that cooperates with a latch surface on the other thereof to hold the two portions connected, wherein said drive element in said second position limits or prevents resilient movement of said moveable latch finger, thereby preventing disconnection of said first and second body portions after operation.

2. An autoinjector according to claim 1, wherein first and second body portions comprise front and rearward generally tubular body portions that are snap fitted together during assembly.

3. An autoinjector according to claim 1, wherein said snap fit arrangement includes a plurality of respective removable latch fingers and latch surfaces.

4. An autoinjector according to claim 3, wherein said drive element blocks at least two of said resiliently moveable latch fingers when in said second position.

5. An arrangement according to claim 1, wherein the latch surface comprises an edge of an aperture in the body.

6. An autoinjector according to claim 1, wherein said drive element is an elongate plunger having a blocking surface for moving into alignment with the resiliently moveable latch finger when in said second position.

7. An autoinjector according to claim 2, wherein said snap fit arrangement includes a plurality of respective removable latch fingers and latch surfaces.

8. An autoinjector according to claim 7, wherein said drive element blocks at least two of said resiliently moveable latch fingers when in said second position.

9. An arrangement according to claim 2, wherein the latch surface comprises an edge of an aperture in the body.

10. An autoinjector according to claim 3, wherein said drive element is an elongate plunger having a blocking surface for moving into alignment with each resiliently moveable latch finger when in said second position.

11. An autoinjector according to claim 1, wherein said drive element is an elongate plunger having a blocking surface that moves into alignment with each resiliently moveable latch finger when drive element moves from the first position to said second position.

12. An autoinjector according to claim 3, wherein said drive element has a blocking surface that is in alignment with each resiliently moveable latch finger when in said second position after the drive element moves from the first position to said second position.

13. An autoinjector comprising:
a body comprising a first body portion and a second body portion,
the first body portion comprising an aperture with an edge that defines a latch surface;
the second body portion comprising a moveable latch finger,
the first body portion and the second body portion being snap-fitted together with the moveable latch finger engaged on the latch surface;
a syringe or cartridge with a needle contained in the body, the syringe or cartridge containing a medicament;
a drive element that, during operation to deliver the medicament, moves from a first position to a second position,
wherein the drive element has a blocking surface,
wherein with the drive element in said first position, the blocking surface of the drive element is non-aligned with the moveable latch finger and does not block movement of the moveable latch finger from the latch surface, and
wherein with the drive element in said second position, the blocking surface of the drive element is aligned with the moveable latch finger and the blocking surface of the drive element blocks movement of the moveable latch finger such that the moveable latch finger is retained engaged on the latch surface thereby preventing disconnection of said first and second body portions.

14. The autoinjector of claim 13, wherein,
the first body portion is a rear assembly containing the drive element, and
the second body portion is a front assembly containing the syringe or cartridge.

15. The autoinjector of claim 13, comprising plural of the aperture with the edge that defines the latch surface and plural of the moveable latch finger,
wherein each moveable latch finger is engaged on a corresponding one of the latch surface;
wherein with the drive element in said first position, the blocking surface of the drive element is non-aligned with each moveable latch finger, and
wherein with the drive element in said second position, the blocking surface of the drive element is aligned with each moveable latch finger and the blocking surface of the drive element blocks movement of each moveable latch finger such that each moveable latch finger is retained engaged on the corresponding one latch surface thereby preventing disconnection of said first and second body portions.

16. The autoinjector of claim 15, wherein,
the first body portion is a rear assembly containing the drive element, and
the second body portion is a front assembly containing the syringe or cartridge.

17. The autoinjector of claim 13, wherein, the drive element is an elongate plunger having the blocking surface that moves into alignment with the resiliently moveable latch finger when in said second position.

18. The autoinjector of claim 15, wherein, the drive element is an elongate plunger having the blocking surface that moves into alignment with each resiliently moveable latch finger when in said second position.

19. An autoinjector comprising:
a body comprising a first body portion and a second body portion,
the first body portion comprising a recess;
the second body portion comprising a moveable latch finger,
the first body portion and the second body portion being snap-fitted together with the moveable latch finger engaged on the recess;
a syringe or cartridge with a needle contained in the body, the syringe or cartridge containing a medicament;
a drive element that, during operation to deliver the medicament, moves from a first position to a second position, wherein the drive element has a blocking surface, wherein with the drive element in said first position, the blocking surface of the drive element is non-aligned with the moveable latch finger and does not block movement of the moveable latch finger from the recess, and wherein with the drive element in said second position, the blocking surface of the drive element is aligned with the moveable latch finger and the blocking surface of the drive element blocks movement of the moveable latch finger such that the moveable latch finger is retained engaged on the recess thereby preventing disconnection of said first and second body portions.

20. The autoinjector of claim 19, comprising at least two of the recess and at least two of the moveable latch finger, wherein each moveable latch finger is engaged on a corresponding one of the at least two recesses, wherein with the drive element in said first position, the blocking surface of the drive element is non-aligned with the at least two moveable latch fingers, and wherein with the drive element in said second position, the blocking surface of the drive element is aligned with the at least two moveable latch fingers and the blocking surface of the drive element blocks movement of the at least two moveable latch fingers such that the at least two moveable latch fingers are retained engaged on the corresponding recess preventing disconnection of said first and second body portions.

\* \* \* \* \*